US00PP14543P29

(12) United States Plant Patent
Noodelijk

(10) Patent No.: US PP14,543 P2
(45) Date of Patent: Feb. 17, 2004

(54) CHRYSANTHEMUM PLANT NAMED 'LUNA'

(50) Latin Name: *Chrysanthemum morifolium*
Varietal Denomination: Luna

(75) Inventor: Robert Noodelijk, Woubrugge (NL)

(73) Assignee: Chrysanthemum Breeders Association, N.V. (NL)

( * ) Notice: Subject to any disclaimer, the term of this patent is extended or adjusted under 35 U.S.C. 154(b) by 0 days.

(21) Appl. No.: 10/316,866

(22) Filed: Dec. 12, 2002

(51) Int. Cl.[7] ..... A01H 5/00
(52) U.S. Cl. ..... Plt./289
(58) Field of Search ..... Plt./289

*Primary Examiner*—Anne Marie Grunberg
(74) *Attorney, Agent, or Firm*—Parkhurst & Wendel, L.L.P.

(57) ABSTRACT

A chrysanthemum plant named 'Luna' characterized by its medium sized blooms with yellow ray florets and prolific branching; natural season flower date August 26–31; blooming for a period of 5 weeks.

3 Drawing Sheets

BACKGROUND OF THE INVENTION

'Luna' is a product of a breeding and selection program for outdoor pot mums (garden mums) which had the objective of creating new chrysanthemum cultivars with a decorative type flower, a natural season flower date around August 26–31; blooming for a period of 5 weeks. The new plant of the present invention comprises a new and distinct cultivar of Chrysanthemum plant 'Luna' is a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout Holland in August 2000. The plant has been asexually reproduced by cuttings in greenhouses at Rijsenhout Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
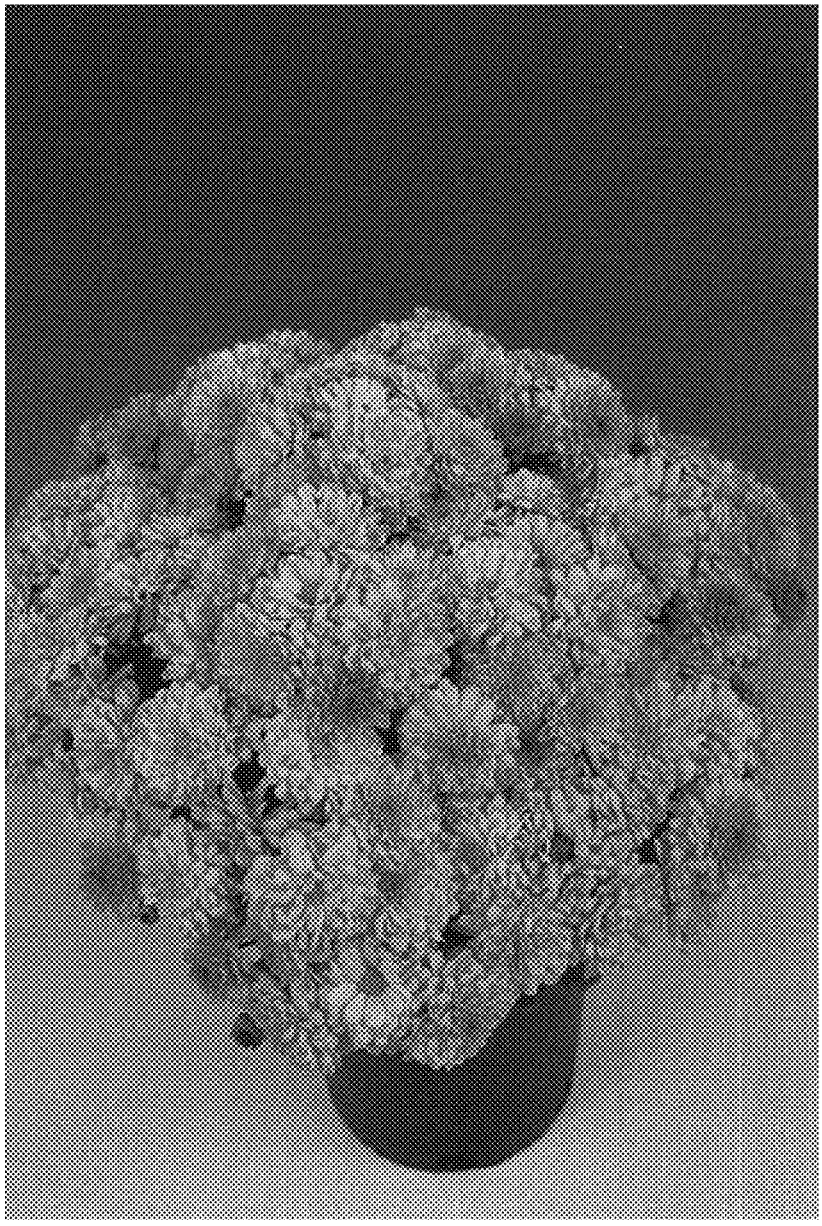
FIG. 1 shows a plant of the cultivar in full bloom.
Figure 2:
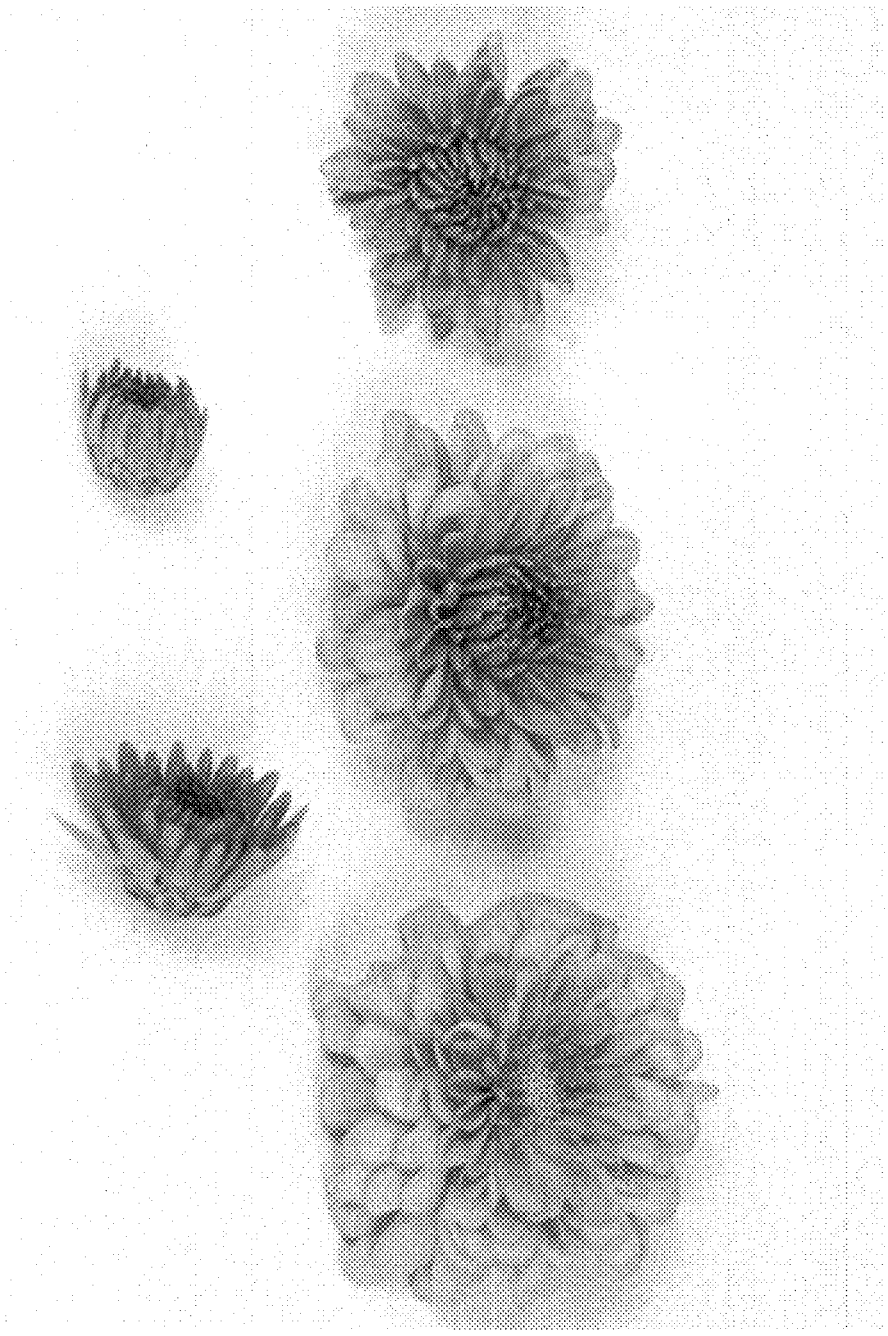
FIG. 2 shows the various stages of bloom of the new cultivar.
Figure 3:
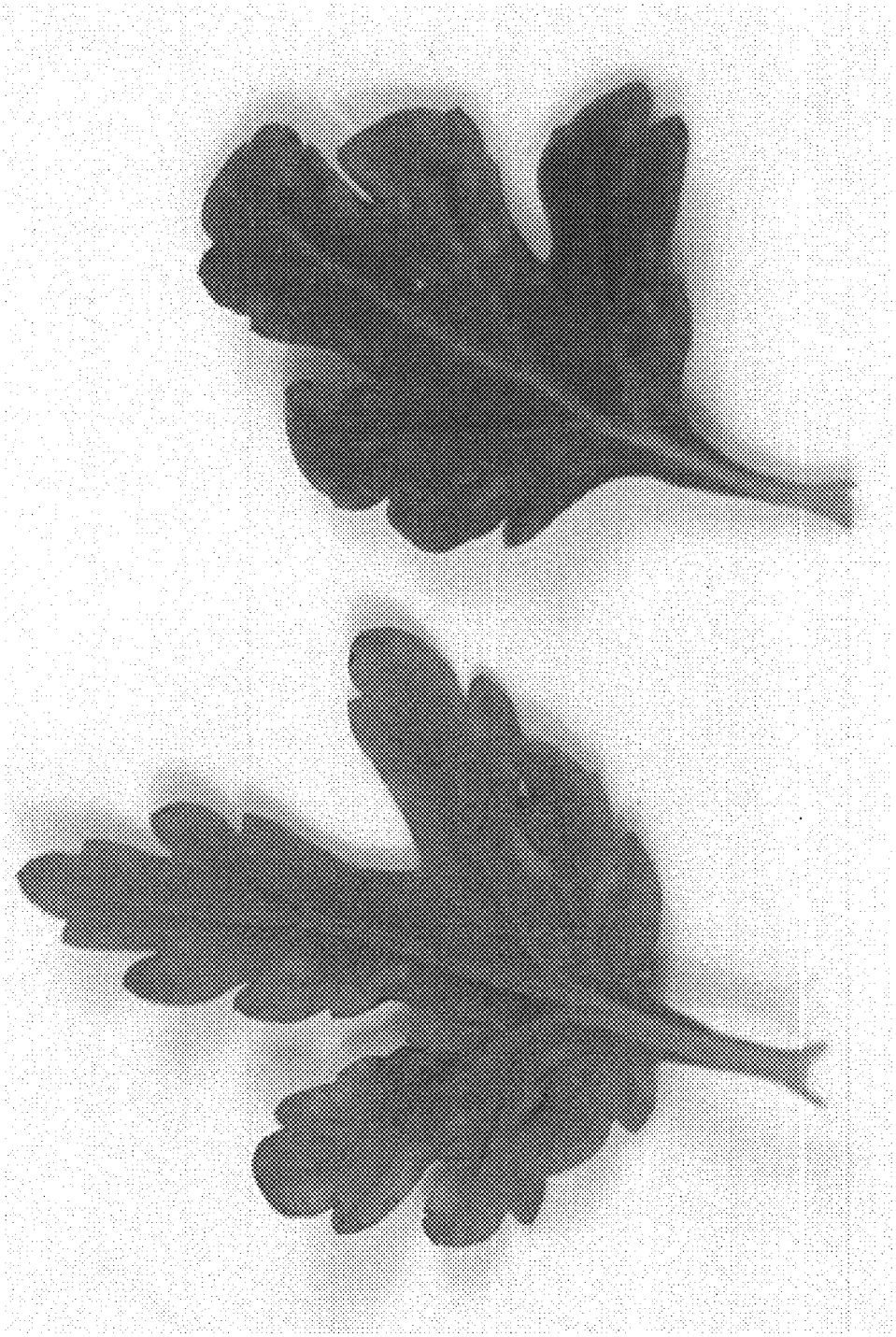
FIG. 3 shows the petiole and foliage of the new cultivar.

This new variety of chrysanthemum is of the botanical classification *Chrysanthemum morifolium*. The observations and measurements were gathered from plants grown out door in Rijsenhout, Holland under natural day length and temperature and planted week 22 in 2000 And 2001. The natural blooming date of this crop was August 26–31 (week 35). The average height of the plants was 23 cms. No growth retardants were used. No tests were done on disease or insect resistance or susceptibility. No tests were done on cold or drought tolerance. This new variety produces medium sized blooms with yellow ray florets and a yellow center blooming for a period of 5 weeks.

From the cultivars known to inventor the most similar existing cultivar in comparison to 'Luna' is 'Feniks' (U.S. Plant patent application Ser. No. 10/316,871). When 'Feniks' and 'Luna' are being compared the following differences are noticed: The differences of 'Feniks' and 'Luna' are (1) Flowerform and color. 'Luna' has a darker colored flower center only when immature; 'Feniks' has a darker colored flower center both in the immature and mature stage. 'Luna' has disc-florets when mature, 'Feniks' has no disc-florets. (2) Natural flowering date. 'Luna' flowers one week earlier than 'Feniks'.

The following is a description of the plant and characteristics that distinguish 'Luna' as a new and distinct variety. The color designations are taken from the plant itself. Accordingly, any discrepancies between the color designations and the colors depicted in the photographs are due to photographic tolerances. The color chart used in this description is: The Royal Horticultural Society colour chart, edition 1995.

Table 1. Botanical Description of Cultivar 'Luna'

Bud:
- *Size.*—Medium ;cross-section 1.4 cm, height 0.9 cm.
- *Outside color.*—Yellow-orange 20 A.
- *Involucral bracts.*—2 rows, length 7 mm, width 3 mm.
- *Involucral bracts among disc-florets.*—Not present.
- *Involucral bracts color.*—Green 138 A.

Bloom:
- *Type.*—Decorative.
- *Height.*—1.0–1.2 cm.
- *Size.*—13 Medium.
- *Fully expanded.*—3.5–4.5 cm.
- *Number of blooms per branch.*—Approx. 6–8 blooms per branch.
- *Performance on the plant.*—5 weeks.
- *Seeds (if crossed).*—Produced in small quantities, ovate grey-brown 199A, 1½ mm in length.
- *Fragrance.*—Typical chrysanthemum, slightly.

Color:
- *Center of the flower (disc-florets when mature).*—Immature yellow-orange 20 A. Mature yellow 14 A.
- *Color of upper surface of the ray-florets.*—Yellow-orange 15 B.

*Color of the lower surface of the ray-florets.*—Yellow-orange 15 A.
*Tonality from distance.*—A garden mum with yellow flowers and a yellow disc.
*Color of the upper surface of the ray-florets after aging of the plant.*—Yellow 14 B.

Ray florets:
*Texture.*—Upper and under side smooth.
*Number.*—140–160.
*Cross-section.*—Convex.
*Longitudinal axis of majority.*—Reflexing.
*Length of corolla tube.*—0.4 cm.
*Ray-floret margin.*—Entire.
*Ray-floret length.*—1.8–2.0 cm.
*Ray-floret width.*—0.5 cm.
*Ratio length/width.*—Medium.
*Shape of tip.*—Rounded.

Disc florets:
Disc diameters.—0.7 cm.
*Distribution of disc florets.*—Numerous, only visible when mature.
*Shape.*—Tubular.
*Color.*—Yellow 14 A.
*Receptacle shape.*—Domed raised.

Reproductive organs:
*Stamen* (*present in disc florets only*).—Thin, 3 mm in lenght.
*Stamen color.*—Yellow-green 144 A.
*Pollen.*—Present.
*Pollen color.*—Yellow 7 A.
*Styles.*—Thin.
*Style color.*—Yellow-green 144 A.
*Style length.*—4 mm.
*Stigma color.*—Yellow-green 144 A.
*Stigma width.*—1 mm.
*Ovaries.*—Enclosed in calyx.

Plant:
*Shape.*—Grown as spray-type pot mum, outdoor mounded and round.
*Growth habit.*—Spreading.
*Growth rate.*—Moderate.
*Height.*—23 cm.
*Width.*—34–36 cm.
*Stem color.*—Yellow-green 148 B.
*Stem strength.*—Strong.
*Stem brittleness.*—Present.
*Stem anthocyanin coloration.*—Absent.
*Length of lateral branch.*—From top to bottom 11–12 cm.
*Lateral branch color.*—Yellow-green 148 B.
*Lateral branch, attachment.*—Brittle.
*Branching* (*average number of lateral branches*).—Good with 6–7 breaks after pinching.
*Peduncle length.*—6–7 cm.
*Peduncle color.*—Yellow-green 148 B.
*Natural season blooming date foliage.*—August 26–31.
*Color.*—Upper side yellow-green 148 A. Under side yellow-green 148 B.
*Size.*—Medium.; length 6.0 cm, width 5.0 cm
*Quantity* (*number per lateral branch*).—7–8.
*Shape.*—Ovate.
*Texture upper side.*—Glabrous.
*Texture under side.*—Pubescent.
*Venation arrangement.*—Palmate.
*Shape of the margin.*—Serrated.
*Shape of base of sinus between lateral lobes.*—Round.
*Margin of sinus between lateral lobes.*—Diverging.
*Shape of base.*—Truncate.
*Apex.*—Mucronate.

TABLE 2

Differences with the comparison varieties

| | 'LUNA' | 'FENIKS' |
|---|---|---|
| Color of the immature flower | Yellow-orange 20 A, at the tips greyed-orange 168 B | Greyed-orange 169 A |
| Color of the mature flower | Yellow 14 A | Greyed-orange 169 A |

I claim:

1. A new and distinct variety of chrysanthemum plant as described and illustrated.

* * * * *